US006446628B1

(12) United States Patent
Chen

(10) Patent No.: US 6,446,628 B1
(45) Date of Patent: Sep. 10, 2002

(54) WATER SUPPLY DEVICE FOR DIVERS

(75) Inventor: Jiunn Liang Chen, Taichung Hsien (TW)

(73) Assignee: Akira Yamaike, Aichi (JP)

( * ) Notice: Subject to any disclaimer, the term of this patent is extended or adjusted under 35 U.S.C. 154(b) by 97 days.

(21) Appl. No.: 09/718,509

(22) Filed: Nov. 24, 2000

(51) Int. Cl.[7] ...................... A61M 15/00; A61M 16/00; A62B 7/00; A62B 9/00; A62B 18/00

(52) U.S. Cl. ........................... 128/200.24; 128/200.25; 222/175; 222/105; 224/148.2; 224/414

(58) Field of Search ...................... 128/200.24, 200.25, 128/200.29, 201.11, 859, 860, 861, 862; 222/144.5, 105, 175, 610; 244/414, 148.2

(56) References Cited

U.S. PATENT DOCUMENTS 4,193,518 A * 3/1980 Holmes ...................... 222/105
4,398,533 A * 8/1983 Barker .................. 128/202.15
4,815,893 A * 3/1989 Feder .................... 128/202.15
5,524,612 A * 6/1996 Chen ..................... 128/200.29
5,634,780 A * 6/1997 Chen ..................... 128/202.15
5,709,478 A * 1/1998 Chen ..................... 128/202.15
5,755,368 A * 5/1998 Bekkedahl .................. 222/175
5,984,145 A * 11/1999 McAllister .................. 222/175
6,283,344 B1 * 9/2001 Bradley ...................... 222/175

* cited by examiner

*Primary Examiner*—John G. Weiss
*Assistant Examiner*—Michael Mendoza
(74) *Attorney, Agent, or Firm*—Rosenberg, Klein & Lee

(57) ABSTRACT

A water supply device for divers includes a cylinder connected to a mouthpiece and a piston member is movably received in the cylinder so that when the piston member is moved by pushing a push rod connected to the piston member, water in the cylinder flows out from the cylinder and enters into the mouthpiece. The piston member has a central passage defined longitudinally therethrough and has a threaded portion defined in a periphery defining the central passage. The push rod extends through the central passage of the piston member and has a threaded section engaged with the threaded portion of the piston member. The push rod is disengaged from the threaded portion of the piston member and received in the cylinder when the push rod is not in use.

5 Claims, 8 Drawing Sheets

WATER SUPPLY DEVICE FOR DIVERS

FIELD OF THE INVENTION

The present invention relates to a water supply device for divers and the device has a push rod threadedly connected to a piston member in a cylinder so that the push rod can be disengaged from the piston member and received in the cylinder when the push rod is not in use.

BACKGROUND OF THE INVENTION

A conventional water supply device known to applicant is disclosed in U.S. Pat. No. 5,524,612 to Chen with a title of "Drinking Device For Drivers", filed Nov., 22, 1994. A mouthpiece is connected to a cylinder which includes a push rod and a cylinder in which water is filled. The push rod can be pushed into the cylinder to squeeze water in the cylinder into the mouthpiece for relief thirsty of the divers. Another water supply device 80 is disclosed in FIG. 8 and has a similar structure as the cylinder in U.S. Pat. No. 5,524,612. The cylinder 81 has a push rod 83 movably inserted therein and a head 831 is connected to the push rod 83 and accessible by the diver. A piston member 85 is mounted to the push rod 83 and located in the cylinder 81. A spring 82 is biased between the piston member 85 and an end of the cylinder 81 so that the piston member 85 is kept at the left extreme position as shown in FIG. 8. When the diver pushes the push rod 83, the piston member 85 pushes the water in the cylinder 81 to flow out from a passage 84 communicating with an interior of the cylinder 81.

Both of the conventional water supply devices shown above involve a push rod that extends outward from the cylinder 81. However, the extending push rod sometimes is not convenient for the divers especially when diving in a narrow space because the push rod could be tangled by objects around the divers.

The present invention intends to provide a water supply device for divers wherein the push rod can be received in the cylinder when it is not to be used.

SUMMARY OF THE INVENTION

In accordance with one aspect of the present invention, there is provided a water supply device and comprising a cylinder connected to a mouthpiece which has a passage communicating with an interior of the cylinder. An inlet is defined radially through the cylinder and a pipe is connected between the inlet and a bladder. A piston member is received in the cylinder and has a central passage defined longitudinally therethrough. A threaded portion is defined in a periphery defining the central passage and a spring is biased between the piston member and a closed end of the cylinder. A push rod extends through the central passage of the piston member and has a threaded section engaged with the threaded portion of the piston member. The push rod can be disengaged from the threaded portion of the piston member and received in the cylinder.

The primary object of the present invention is to provide a water supply device for divers wherein the push rod of the device can be received in the cylinder so that the push rod will not tangle objects.

These and further objects, features and advantages of the present invention will become more obvious from the following description when taken in connection with the accompanying drawings which show, for purposes of illustration only, several embodiments in accordance with the present invention.

DETAILED DESCRIPTION OF THE PREFERRED EMBODIMENT

Figure 1:
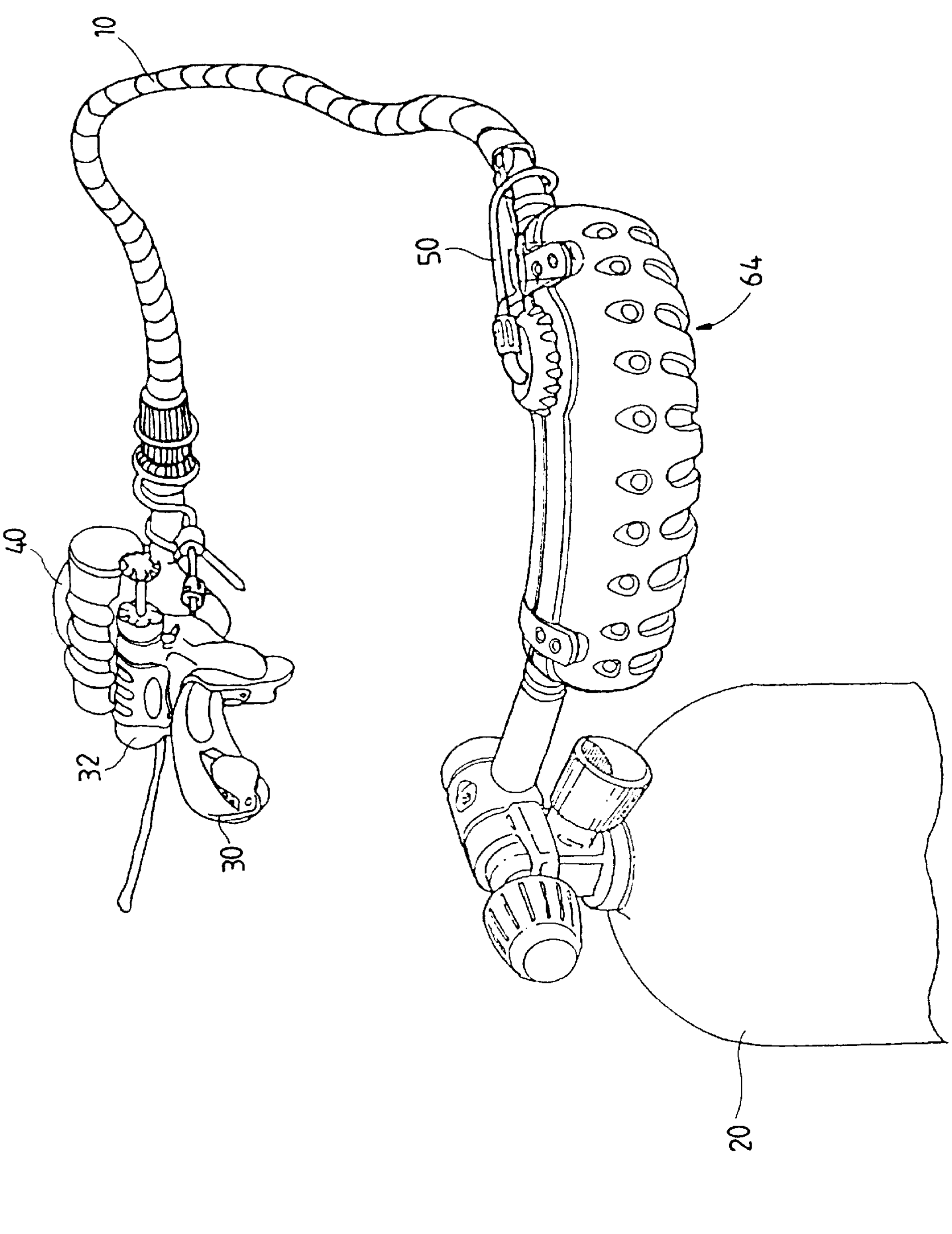
FIG. 1 is a perspective view to show a oxygen cylinder connected to a mouthpiece with a water supply device of the present invention.
Figure 2:
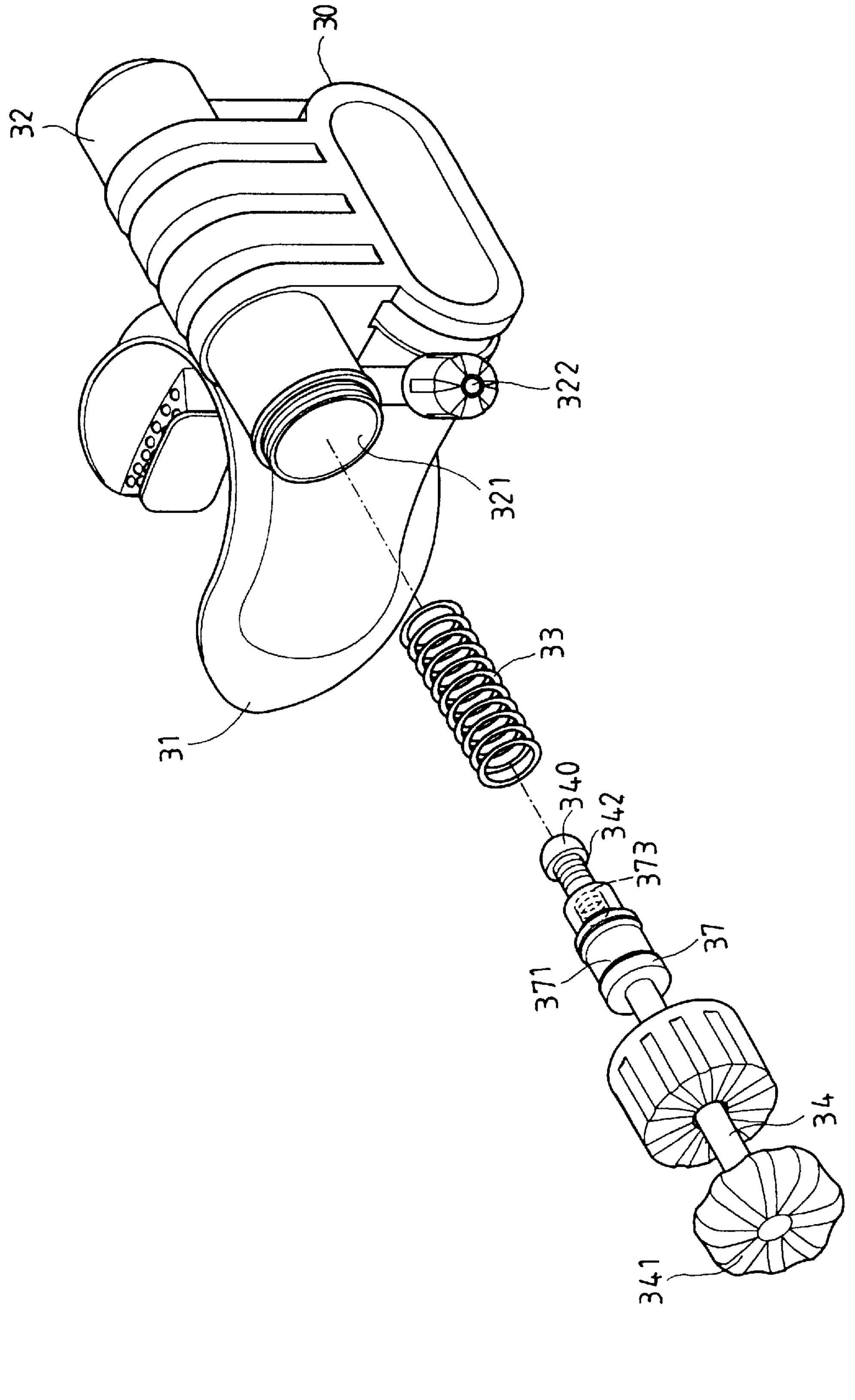
FIG. 2 is an exploded view to show the water supply device of the present invention.
Figure 3:
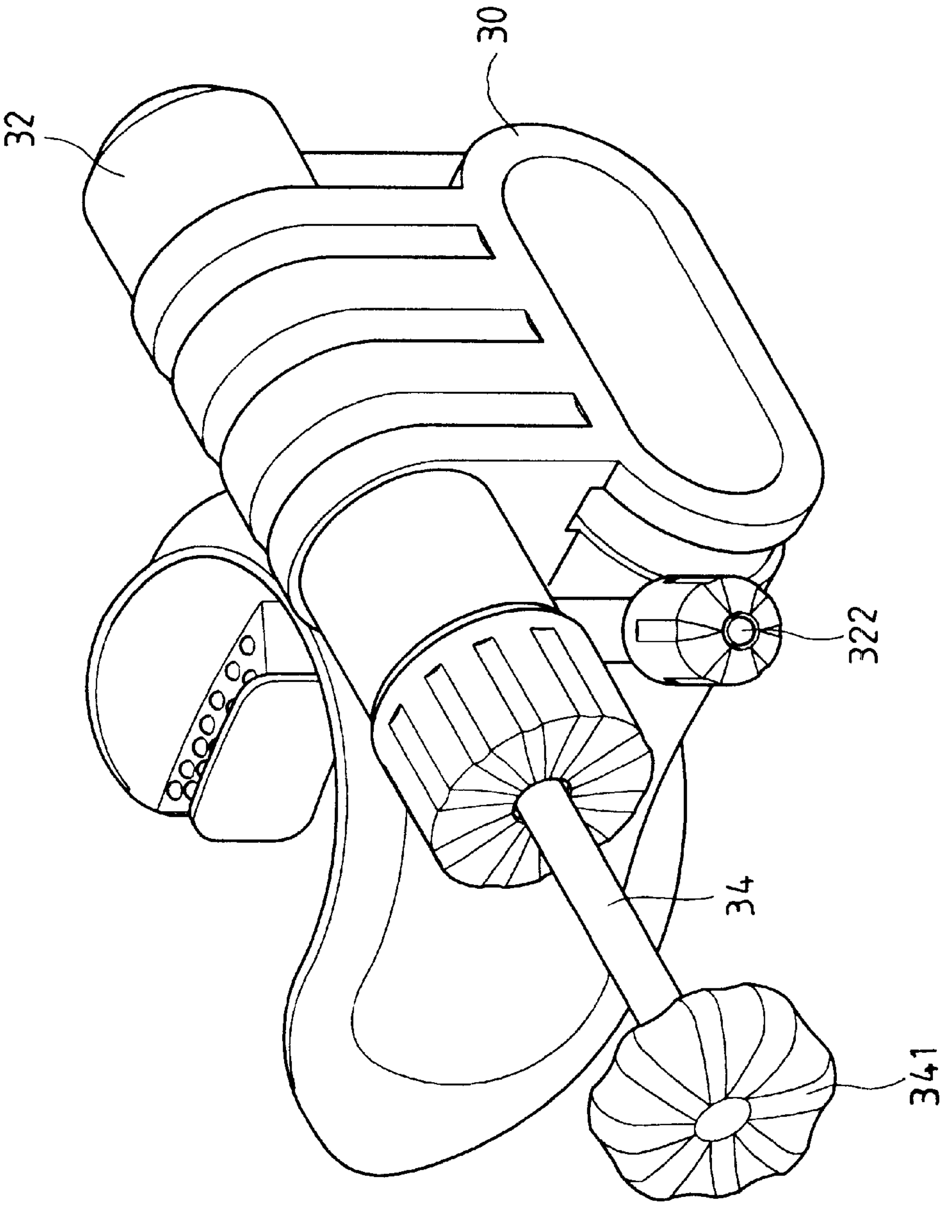
FIG. 3 is a perspective view to show the water supply device of the present invention.
Figure 4:
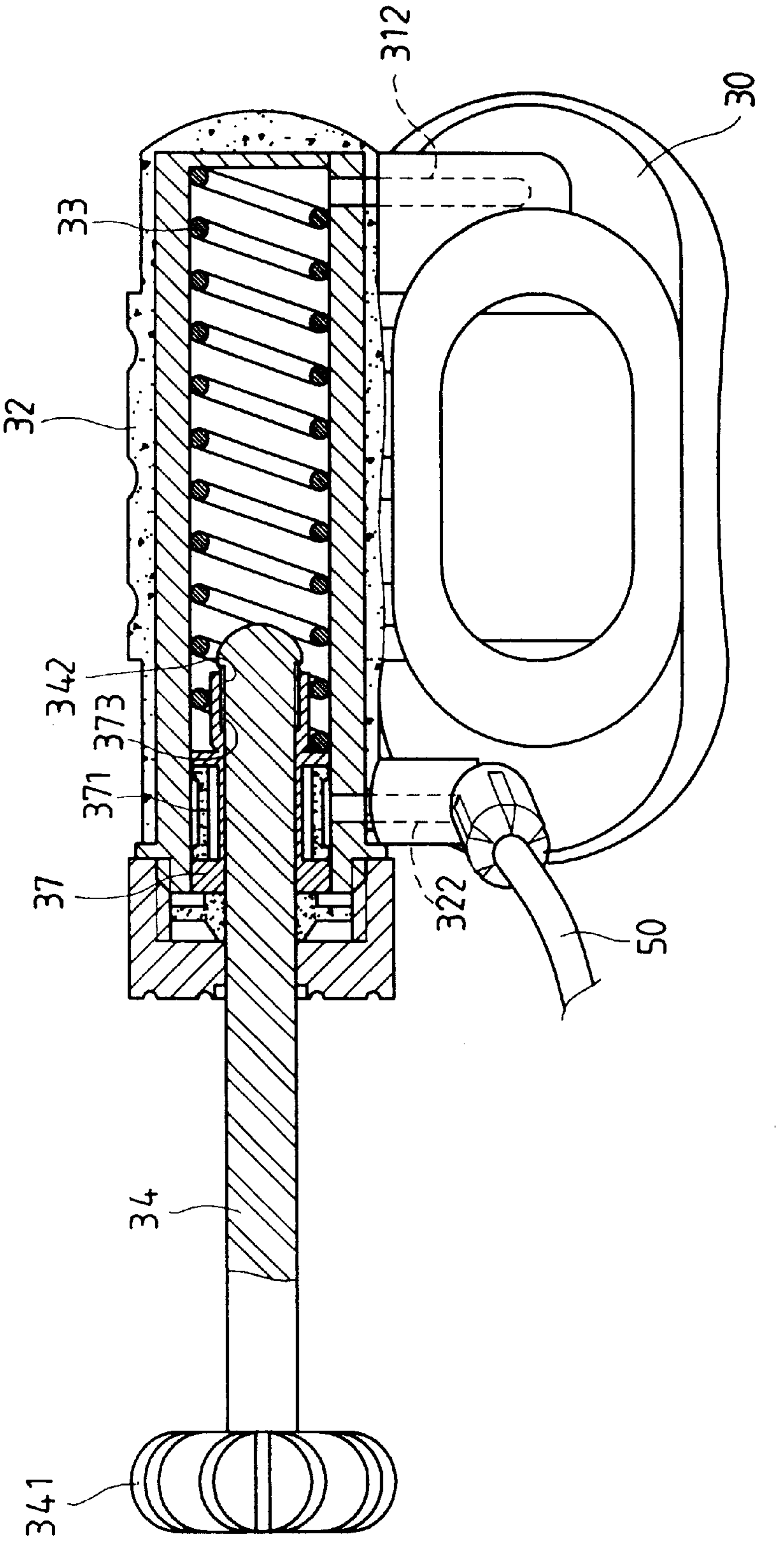
FIG. 4 is a cross sectional view to show the water supply device of the Present invention.

Referring to FIGS. 1 to 4, the water supply device for divers of the present invention comprises a cylinder 32 connected to a mouthpiece 30 which has a passage 312 defined therein and the passage 312 communicates with an interior of the cylinder 32 so that water in the cylinder 32 can be pushed into the diver's mouth via the passage 312. The cylinder 32 has a closed end and an open end through which a spring 33 is received and an inlet 322 is defined radially through the cylinder 32 and a pipe 50 engaged with the inlet 322. A bladder 61 (see FIG. 7) is connected to the pipe 50 so as to provide water to the cylinder 32.

A piston member 37 is received in the cylinder 32 and has a central passage defined longitudinally therethrough. Seals 371 are mounted to the piston member 37 so that the piston member 37 is movably engaged with an inner periphery of the passage 312. The spring 33 is biased between the piston member and the closed end of the cylinder 32. A threaded portion 373 is defined in a periphery defining the central passage.

A push rod 34 extends through the central passage of the piston member 37 and a threaded section 342 is defined in an outer periphery of the push rod 34. The threaded section 342 is engaged with the threaded portion 373 of the piston member 37 and a head 340 is connected to a distal end of the push rod 34. The head 340 is larger than a diameter of the central passage of the piston member 37 so that the push rod 34 will not slide off from the central passage of the piston member 37. The other distal end of the push rod 34 has an operation knob 341 for convenience of push by the divers.

Figure 5:
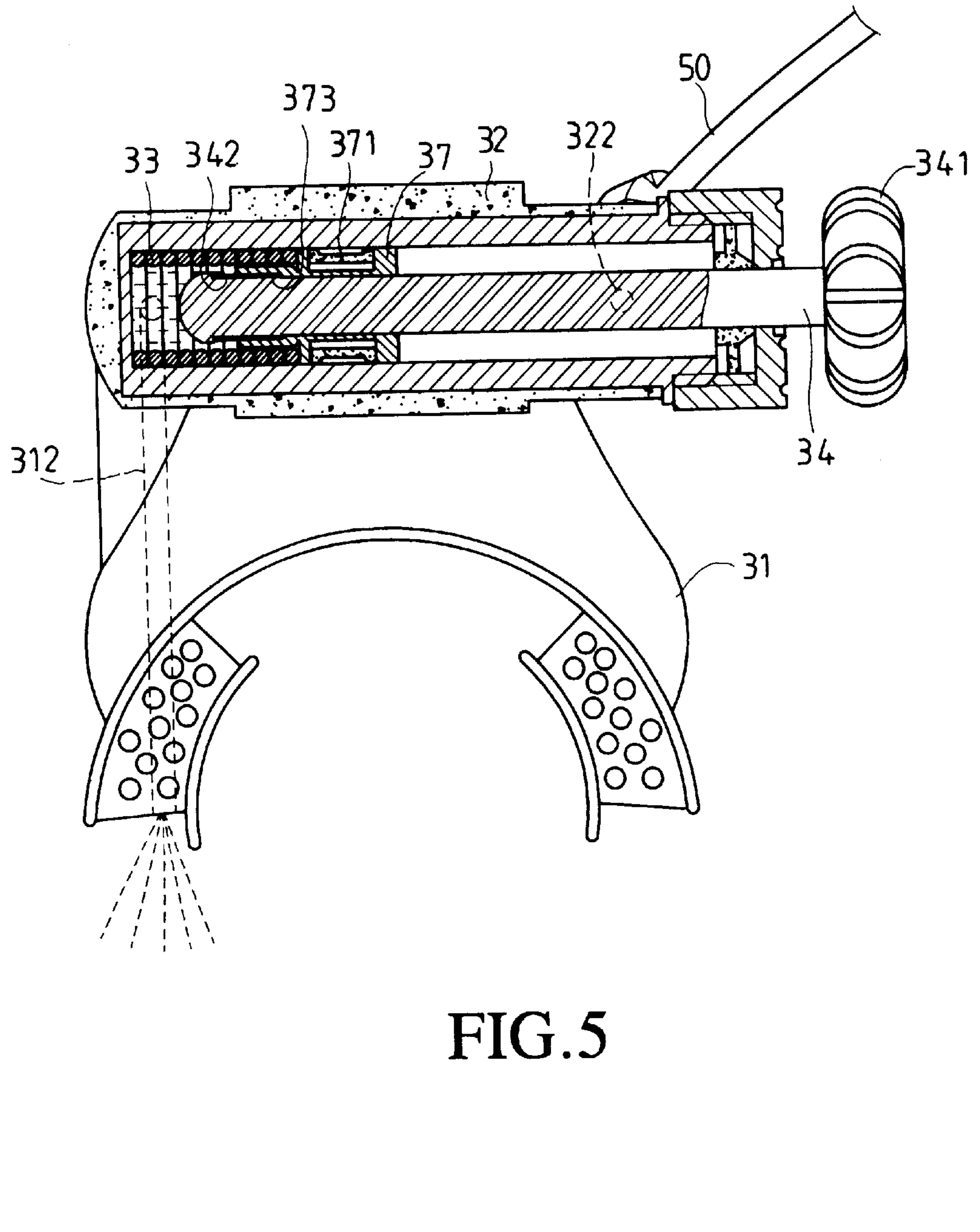
FIG. 5 is a cross sectional view to show the water in the cylinder is ejected from the mouthpiece by pushing the push rod of the supply device of the present invention.
Figure 6:
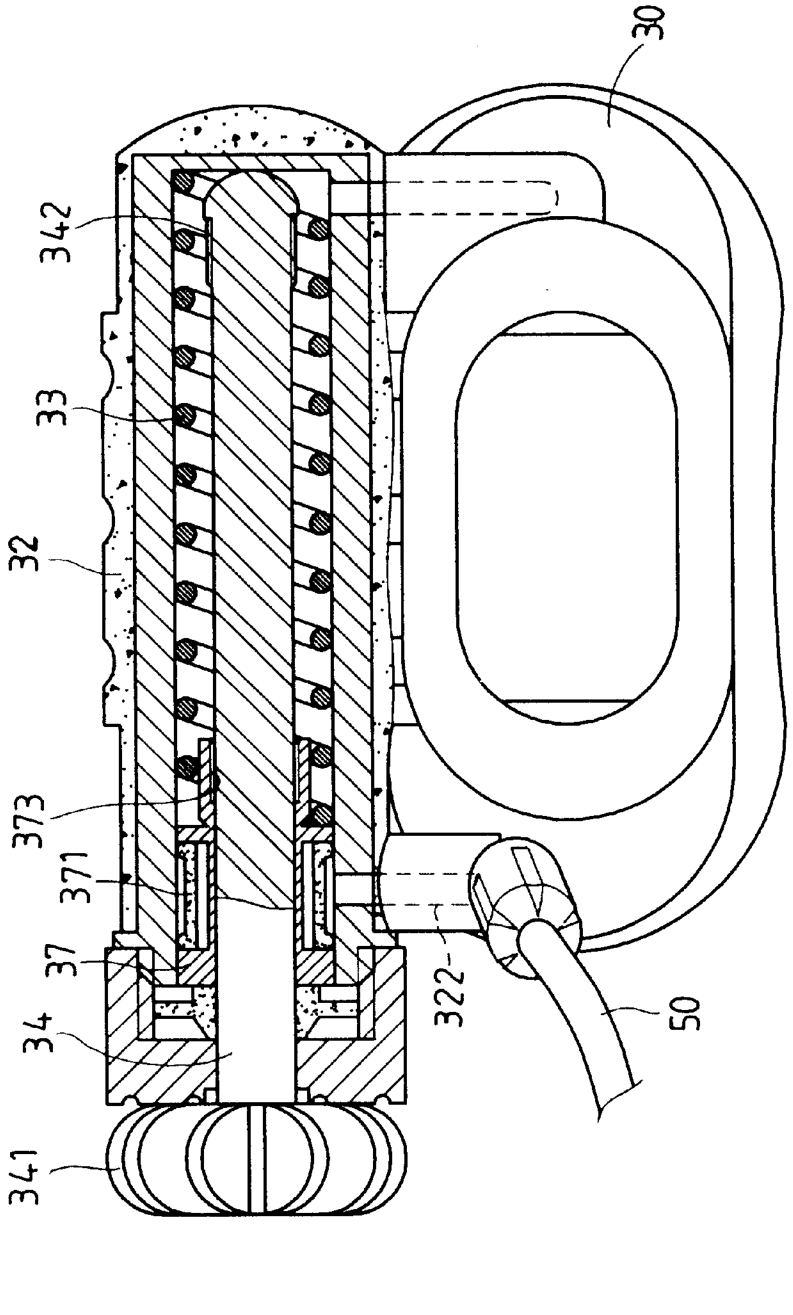
FIG. 6 is a cross sectional view to show the push rod of the water supply device of the present invention is received in the cylinder.

As shown in FIG. 5, when pushing the operation knob 341 toward the cylinder 32, water in the cylinder 32 is pushed by the piston member 37 and ejected out from the mouthpiece 30 via the passage 312 and enters in the diver's mouth. When releasing the push rod 34, the spring 33 pushes the push rod 34 to its original position. As shown in FIG. 6, when the push rod 34 is not in use, the push rod 34 is rotated to disengage from the threaded portion 342 so that the push rod 34 can be received in the cylinder 32 as shown. When the push rod 34 is received in the cylinder 32, it will not tangled with objects.

Figure 7:
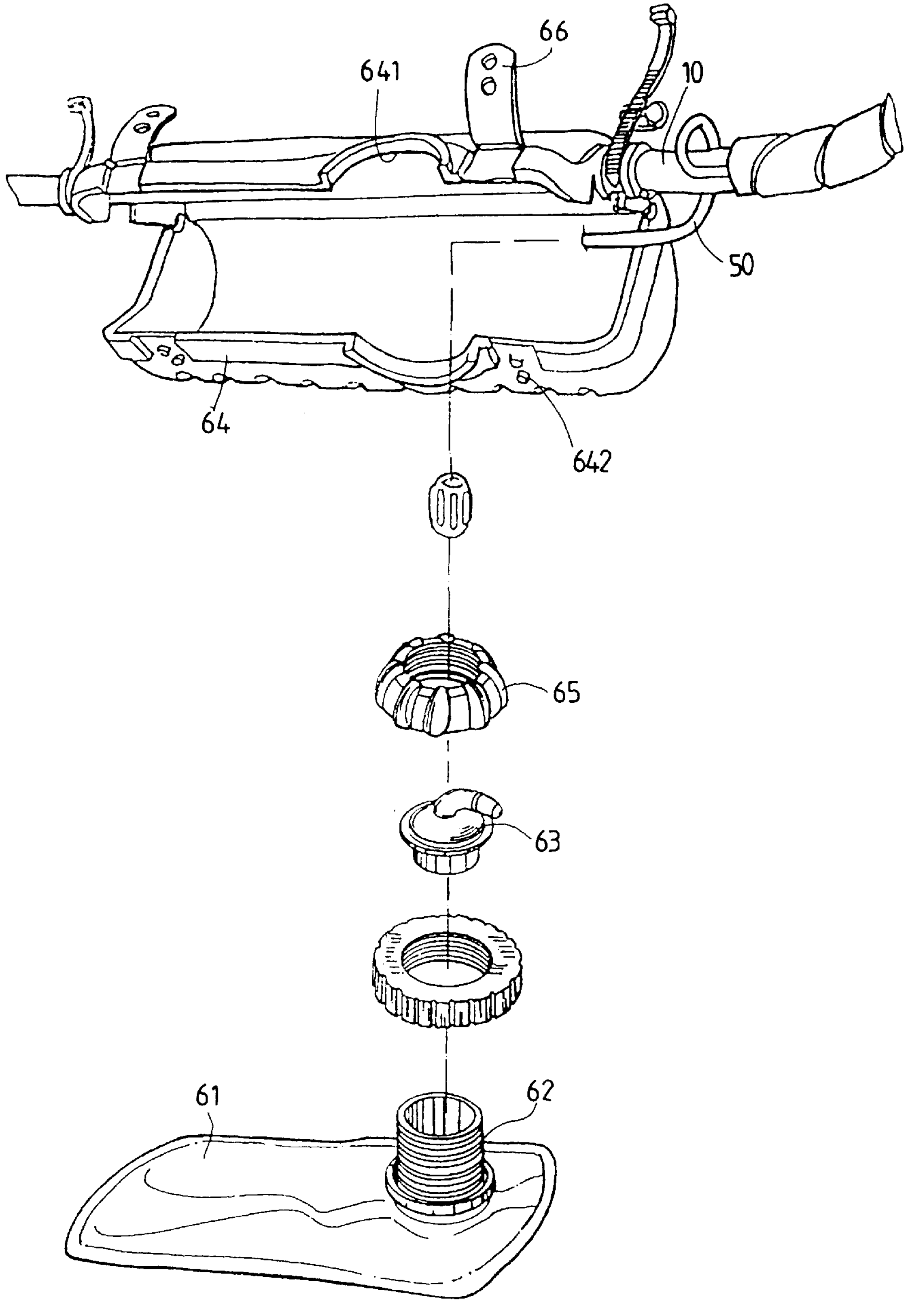
FIG. 7 is an exploded view to show a water bladder connected to the water supply device of the present invention.
Figure 8:
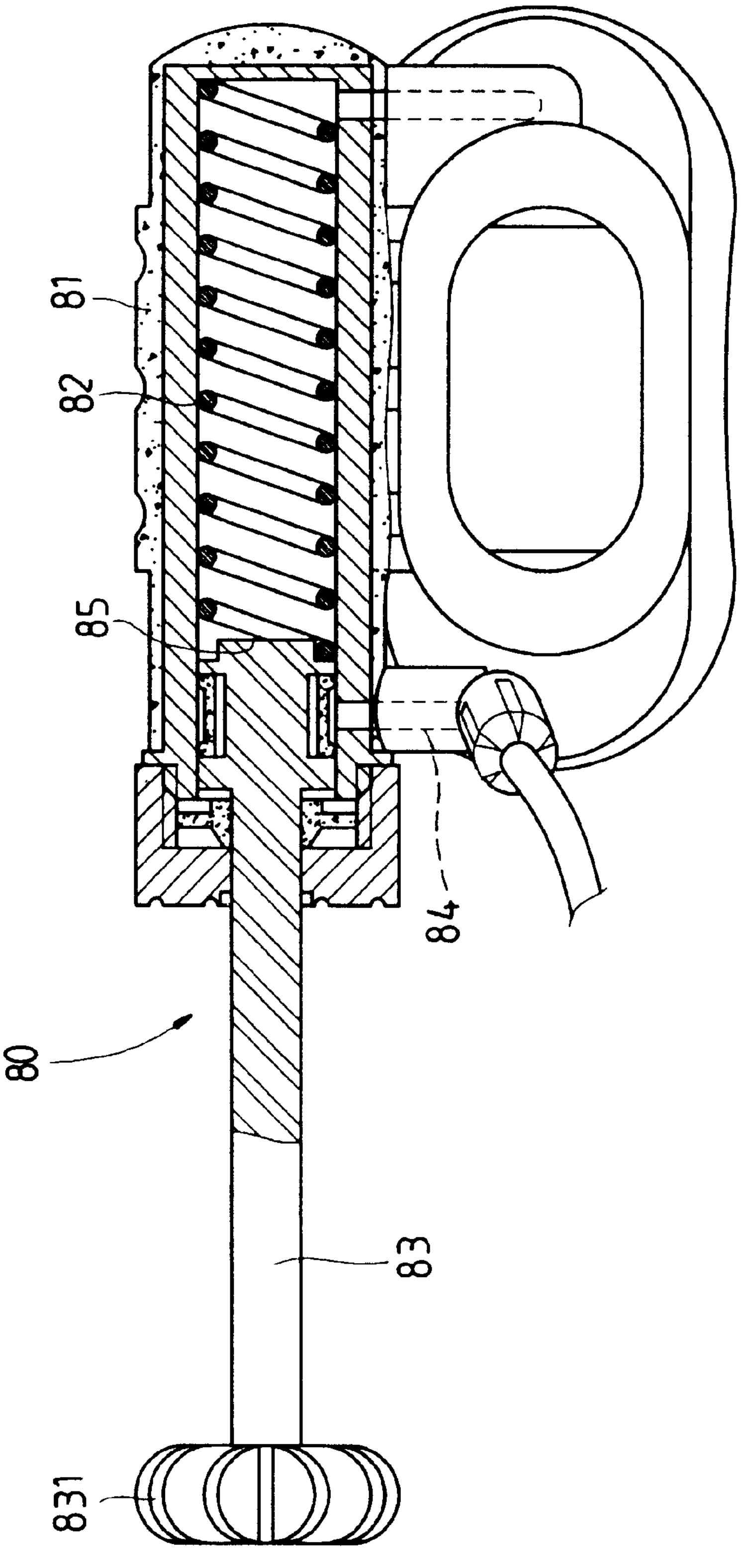
FIG.8 PRIOR ART
FIG. 8 is a cross sectional view to show a conventional water supply device for divers.

Referring to FIGS. 1 and 7, an oxygen pipe 10 is connected between the oxygen cylinder 20 and a regulator 40 connected to the mouthpiece 30 to provide oxygen to the diver. The bladder 61 is received in a casing 64 which is attached to the oxygen pipe 10. A threaded neck 62 extends from the bladder 61 and communicates with an interior of the bladder 61. A cap 63 is connected to the threaded neck 62 and retained by a retaining collar 65 which is threadedly engaged with the threaded neck 62. The cap 63 is connected to the pipe 50. The casing 64 for receiving the bladder 61 is composed of two parts which are pivotally connected with each other. Each part has a semi-circular recess 641 and the threaded neck 62 extends out from a hole defined by the two semi-circular recesses 641 so that the bladder 61 is protected and received in the casing 64. One of the two parts has a belt 66 through which apertures are defined, and the other part has bosses 642 extending from an outer surface thereof so that the bosses 642 are engaged with the apertures in the belt 66 to connect the two parts.

The engagement of the push rod 34 and the piston member 37 is easily to be disengaged and/or connected simply by rotating the push rod 34 so that when the diver receives the push rod 34 in the cylinder 32, the push rod 34 is avoided to be tangled or broken by objects.

While we have shown and described various embodiments in accordance with the present invention, it should be clear to those skilled in the art that further embodiments may be made without departing from the scope and spirit of the present invention.

What is claimed is:

1. A water supply device comprising:

a cylinder connected to a mouthpiece which has a passage defined therein and the passage communicates with an interior of said cylinder, said cylinder having a closed end and an open end through which a spring is received, an inlet defined radially through said cylinder and a pipe engaged with said inlet, a bladder connected to said pipe;

a piston member received in said cylinder and having a central passage defined longitudinally therethrough, said piston member engaged with an inner periphery of said passage and having a threaded portion defined in a periphery defining said central passage, said spring biased between said piston member and said closed end of said cylinder, and a push rod extending through said central passage of said piston member and having a threaded section defined in an outer periphery of said push rod, said threaded section engaged with said threaded portion of said piston member.

2. The device as claimed in claim 1 further comprising a head connected to a distal end of said push rod and said head being larger than a diameter of said central passage of said piston member.

3. The device as claimed in claim 1 further comprising a threaded neck extending from said bladder and communicating with an interior of said bladder, a cap connected to said threaded neck and retained by a retaining collar threadedly engaged with said threaded neck, said cap connected to said pipe.

4. The device as claimed in claim 3 further comprising a casing for receiving said bladder, said casing having two parts which are pivotally connected with each other, each part having a semi-circular recess and said threaded neck extending from a hole defined by said two semi-circular recesses.

5. The device as claimed in claim 4 wherein one of said two parts has a belt through which apertures are defined, the other part having bosses extending from an outer surface thereof so that said bosses are engaged with said apertures in said belt to connect said two parts.

* * * * *